(12) United States Patent
Pynson

(10) Patent No.: US 8,252,053 B2
(45) Date of Patent: Aug. 28, 2012

(54) INTRAOCULAR LENS INJECTOR APPARATUS AND METHODS OF USE

(75) Inventor: Joel Pynson, Toulouse (FR)

(73) Assignee: Bausch & Lomb Incorporated, Rochester, NY (US)

( * ) Notice: Subject to any disclaimer, the term of this patent is extended or adjusted under 35 U.S.C. 154(b) by 46 days.

(21) Appl. No.: 13/005,220

(22) Filed: Jan. 12, 2011

(65) Prior Publication Data

US 2011/0112545 A1    May 12, 2011

Related U.S. Application Data

(62) Division of application No. 11/610,056, filed on Dec. 13, 2006, now Pat. No. 7,879,090.

(51) Int. Cl.
*A61F 2/16* (2006.01)
(52) U.S. Cl. .................. 623/6.12; 606/107
(58) Field of Classification Search .......... 623/6.11, 623/6.12, 6.13; 606/107, 108; 604/57, 59, 604/60
See application file for complete search history.

(56) References Cited

U.S. PATENT DOCUMENTS

| | | | |
|---|---|---|---|
| 4,122,556 A | 10/1978 | Poler | |
| 4,136,406 A | 1/1979 | Norris | |
| 4,257,521 A | 3/1981 | Poler | |
| 4,312,433 A | 1/1982 | Bopp | |
| 4,326,306 A | 4/1982 | Poler | |
| 4,423,809 A | 1/1984 | Mazzocco | |
| 4,681,102 A * | 7/1987 | Bartell | 606/1 |
| 4,697,697 A | 10/1987 | Graham et al. | |
| 4,765,329 A | 8/1988 | Cumming et al. | |
| 4,787,904 A | 11/1988 | Severin et al. | |
| 4,834,094 A | 5/1989 | Patton et al. | |
| 4,844,242 A | 7/1989 | Chen et al. | |
| 4,950,289 A | 8/1990 | Krasner | |
| 5,131,532 A | 7/1992 | Ives | |
| 5,281,227 A | 1/1994 | Sussman | |
| 5,290,293 A | 3/1994 | Van Noy et al. | |
| 5,354,333 A | 10/1994 | Kammann et al. | |
| 5,425,734 A * | 6/1995 | Blake | 606/107 |
| 5,454,818 A | 10/1995 | Hambleton et al. | |

(Continued)

FOREIGN PATENT DOCUMENTS

DE    3610925 C2    11/1994

(Continued)

OTHER PUBLICATIONS

Pynson, "U.S. Appl. No. 11/610,051, filed Dec. 13, 2006, not yet published,".

(Continued)

*Primary Examiner* — Victor Nguyen
*Assistant Examiner* — David Eastwood
(74) *Attorney, Agent, or Firm* — Jeffrey B. Powers

(57) ABSTRACT

An IOL injector kit comprising a first body portion having a first lumen disposed therethrough, a proximal end, a distal end configured to deposit an IOL into an eye, a second body portion having a second lumen disposed therethrough, a proximal end and distal end, a container comprising a wall defining a container lumen, a first open end configured to receive the proximal end of the first body portion into the container lumen, and a second open end configured to receive the distal end of the second body portion into the container lumen, and an IOL disposed inside said container.

9 Claims, 2 Drawing Sheets

U.S. PATENT DOCUMENTS

| | | |
|---|---|---|
| 5,468,246 A | 11/1995 | Blake |
| 5,494,484 A | 2/1996 | Feingold |
| 5,578,042 A | 11/1996 | Cumming |
| 5,607,433 A | 3/1997 | Polla et al. |
| 5,728,102 A | 3/1998 | Feingold et al. |
| 5,803,925 A | 9/1998 | Yang et al. |
| 5,807,400 A | 9/1998 | Chambers et al. |
| 5,873,879 A | 2/1999 | Figueroa et al. |
| 5,876,406 A | 3/1999 | Wolf et al. |
| 5,884,262 A | 3/1999 | Wise et al. |
| 5,928,245 A | 7/1999 | Wolf et al. |
| 5,944,725 A | 8/1999 | Cicenas et al. |
| 5,947,975 A | 9/1999 | Kikuchi et al. |
| 6,001,107 A | 12/1999 | Feingold |
| 6,162,229 A | 12/2000 | Feingold et al. |
| 6,183,513 B1 | 2/2001 | Guenthner et al. |
| 6,248,111 B1 | 6/2001 | Glick et al. |
| 6,280,449 B1 | 8/2001 | Blake |
| 6,312,433 B1 | 11/2001 | Butts et al. |
| 6,336,932 B1 | 1/2002 | Figueroa et al. |
| 6,355,046 B2 | 3/2002 | Kikuchi et al. |
| 6,387,101 B1 | 5/2002 | Butts et al. |
| 6,398,789 B1 | 6/2002 | Capetan |
| 6,406,481 B2 | 6/2002 | Feingold et al. |
| 6,436,068 B1 | 8/2002 | Gardy |
| 6,447,520 B1 | 9/2002 | Ott et al. |
| 6,468,282 B2 | 10/2002 | Kikuchi et al. |
| 6,471,708 B2 | 10/2002 | Green |
| 6,491,697 B1 | 12/2002 | Clark et al. |
| 6,497,708 B1 | 12/2002 | Cumming |
| 6,500,181 B1 | 12/2002 | Portney |
| 6,503,275 B1 | 1/2003 | Cumming |
| 6,506,195 B2 | 1/2003 | Chambers et al. |
| 6,537,283 B2 | 3/2003 | Van Noy |
| 6,558,395 B2 | 5/2003 | Hjertman et al. |
| 6,605,093 B1 | 8/2003 | Blake |
| 6,629,979 B1 | 10/2003 | Feingold et al. |
| 6,733,507 B2 | 5/2004 | McNicholas et al. |
| 6,858,033 B2 | 2/2005 | Kobayashi |
| 6,923,815 B2 | 8/2005 | Brady et al. |
| 2001/0007942 A1 | 7/2001 | Kikuchi et al. |
| 2001/0020171 A1 | 9/2001 | Heyman et al. |
| 2001/0041897 A1 | 11/2001 | Feingold et al. |
| 2002/0022881 A1 | 2/2002 | Figueroa et al. |
| 2002/0165610 A1 | 11/2002 | Waldock |
| 2003/0212406 A1 | 11/2003 | Kobayashi et al. |
| 2004/0015235 A1 | 1/2004 | Worst et al. |
| 2004/0097957 A1 | 5/2004 | Jaker et al. |
| 2004/0116936 A1 | 6/2004 | Seil |
| 2004/0117012 A1 | 6/2004 | Vincent |
| 2004/0127911 A1 | 7/2004 | Figueroa et al. |
| 2004/0193263 A1 | 9/2004 | Bryan |
| 2004/0215207 A1 | 10/2004 | Cumming |
| 2004/0238392 A1 | 12/2004 | Peterson et al. |
| 2004/0243141 A1 | 12/2004 | Brown et al. |
| 2005/0049605 A1 | 3/2005 | Vaquero et al. |
| 2005/0049606 A1 | 3/2005 | Vaquero et al. |
| 2005/0149058 A1 | 7/2005 | Lin et al. |
| 2005/0182419 A1 | 8/2005 | Tsai |
| 2005/0222579 A1 | 10/2005 | Vaquero et al. |
| 2005/0256528 A1 | 11/2005 | Beavers et al. |
| 2005/0261703 A1 | 11/2005 | Feingold et al. |
| 2005/0277944 A1 | 12/2005 | Kappelhof et al. |
| 2005/0283162 A1 | 12/2005 | Stratas |
| 2006/0085013 A1 | 4/2006 | Dusek et al. |
| 2006/0142780 A1 | 6/2006 | Pynson et al. |
| 2006/0142781 A1 | 6/2006 | Pynson et al. |
| 2007/0055370 A1 | 3/2007 | Sorochkin et al. |
| 2007/0060925 A1 | 3/2007 | Pynson |

FOREIGN PATENT DOCUMENTS

| | | |
|---|---|---|
| DE | 10015472 A1 | 10/2001 |
| DE | 20204172 U1 | 8/2002 |
| DE | 20219445 U1 | 4/2003 |
| DE | 20313283 U1 | 1/2004 |
| DE | 202004009556 U1 | 10/2004 |
| DE | 202005009089 U1 | 9/2005 |
| EP | 0363213 A3 | 4/1990 |
| EP | 0519282 A1 | 12/1992 |
| EP | 1360944 A2 | 11/2003 |
| EP | 1438929 A1 | 11/2003 |
| EP | 1502559 B1 | 2/2005 |
| EP | 1593355 A3 | 11/2006 |
| FR | 2749752 A1 | 12/1997 |
| FR | 2848182 A1 | 6/2004 |
| FR | 2869794 B1 | 11/2005 |
| FR | 2873914 A1 | 2/2006 |
| FR | 2875125 B1 | 3/2006 |
| FR | 2875126 A1 | 3/2006 |
| GB | 2405344 A | 3/2005 |
| JP | 2001340374 A1 | 12/2001 |
| JP | 2002291777 A | 10/2002 |
| JP | 2004041271 A | 2/2004 |
| JP | 2004261263 A1 | 9/2004 |
| JP | 2004344478 A | 12/2004 |
| JP | 2005087771 A | 4/2005 |
| JP | 2005110924 A | 4/2005 |
| JP | 2005131147 A | 5/2005 |
| JP | 2006006817 A | 1/2006 |
| JP | 2006068441 A | 3/2006 |
| WO | WO 99/21513 A1 | 5/1999 |
| WO | WO 99/33411 A1 | 7/1999 |
| WO | WO 01/64147 A1 | 9/2001 |
| WO | WO 2004/010903 A1 | 2/2004 |
| WO | WO 2004/052241 A | 6/2004 |
| WO | WO 2004/105648 A1 | 12/2004 |
| WO | WO 2004/105649 A1 | 12/2004 |
| WO | WO 2005/025459 A1 | 3/2005 |
| WO | WO 2005/030097 A1 | 4/2005 |
| WO | WO 2005/065588 A1 | 7/2005 |
| WO | WO 2005/065589 A1 | 7/2005 |
| WO | WO 2005/070341 A1 | 8/2005 |
| WO | WO 2005/082284 A1 | 9/2005 |
| WO | WO 2005/082285 A1 | 9/2005 |
| WO | WO 2005/084588 A1 | 9/2005 |
| WO | WO 2005/102223 A1 | 11/2005 |

OTHER PUBLICATIONS

Pynson, "U.S. Appl. No. 11/610,057, filed Dec. 13, 2006, not yet published,".

International Search Report (PCT/ISA/210) and Written Opinion (PCT/ISA/237) mailed on May 8, 2008.

* cited by examiner

INTRAOCULAR LENS INJECTOR APPARATUS AND METHODS OF USE

SUMMARY

This application is a divisional of application Ser. No. 11/610056, which was filed Dec. 13, 2006.

FIELD OF INVENTION

The present invention relates to intraocular lens (IOL) injector apparatus and methods of use, and more particularly to apparatus and methods for facilitating loading an IOL.

BACKGROUND OF THE INVENTION

IOLs are artificial lenses used to replace natural crystalline lenses of patients' when their natural lenses are diseased or otherwise impaired. Under some circumstances a natural lens may remain in a patient's eye together with an implanted IOL. IOLs may be placed in either the posterior chamber or the anterior chamber of an eye. IOLs come in a variety of configurations and materials.

Various instruments and methods for implanting such IOLs in an eye are known. Typically, an incision is made in a patient's cornea and an IOL is inserted into the eye through the incision. In one technique, a surgeon uses surgical forceps to grasp the IOL and insert it through the incision into the eye. While this technique is still practiced today, more and more surgeons are using IOL injectors, which offer advantages such as affording a surgeon more control when inserting an IOL into an eye and permitting insertion of IOLs through smaller corneal incisions. Relatively small incision sizes (e.g., less than about 3 mm) are preferred over relatively large incisions (e.g., about 3.2 to 5+mm) since smaller incisions have been attributed with reduced post-surgical healing time and reduced complications such as induced astigmatism.

In order for an IOL to fit through a small incision, it is typically folded and/or compressed prior to entering the eye where it will assume its original unfolded/uncompressed shape. Since IOLs are very small and delicate articles of manufacture, great care is taken in their handling, both as they are loaded into an injector and as the IOLs are injected into patients' eyes.

It is desirable that an IOL be expelled from the tip of the IOL injector and into the eye in an undamaged condition and in a predictable orientation. Should an IOL be damaged or expelled from the injector in an incorrect orientation, a surgeon may need to remove or further manipulate the IOL in the eye, possibly resulting in trauma to the surrounding tissues of the eye. To achieve proper delivery of an IOL, consistent loading of the IOL into the injector device with limited opportunity for damaging the IOL is desirable. Various IOL injectors and other devices have been proposed which attempt to address issues related to loading, yet there remains a need for an IOL injector that improves ease and consistency of loading.

SUMMARY

An aspect of the invention is directed to an IOL injector kit comprising (1) a distal body portion having a first lumen disposed therethrough, a proximal end, a distal end configured to deposit an IOL into an eye, (2) a proximal body portion having a second lumen disposed therethrough, a proximal end and a distal end, (3) a container comprising a wall defining a container lumen, a first open end configured to receive the proximal end of the distal body portion into the container lumen, and a second open end configured to receive the distal end of the proximal body portion into the container lumen, and (4) the IOL disposed inside said container.

In some embodiments, the container further comprises a first end cover and a second end cover configured and arranged to seal said first open end and said second open end, respectively. In some embodiments, the kit further comprises an IOL holding apparatus disposed inside the container and maintaining the IOL, the holding apparatus having a proximal end and the distal end. In some embodiments, the holding apparatus and the distal body portion are configured such that the proximal end of the distal body portion connects to the distal end of the holding apparatus, and the holding apparatus and the proximal body portion are configured such that the distal end of the proximal body portion connects to the proximal end of the holding apparatus.

The kit may comprise a plunger. The plunger may be connected to the proximal body portion. In some embodiments, the distal body portion is configured to fold the IOL as the IOL passes through the first lumen. In some embodiments, the components of a kit may be packaged in a single sterile container. In other embodiments, a plurality of sterile containers may be used, each maintaining one or more components. In embodiments, in which a plurality of sterile containers are used, the sterile containers may be further packaged in a non-sterile container such as a cardboard container.

Another aspect of the invention is directed to a method of loading an IOL injector comprising a proximal body portion and a distal body portion with an IOL, the method comprising (1) providing a container containing an IOL, the container comprising a first end of the container and a second end of the container, and a container lumen, (2) inserting the proximal body portion into the container lumen through the first end, and (3) inserting the distal body portion into the container lumen through the second end.

In some embodiments, the step of providing the container comprises providing the container in a sealed state, the container comprising a first end cover to seal the first end of the container and a second end cover to seal the second end of the container. The method may further comprise removing the first end cover prior to the step of inserting the proximal body portion. In some embodiments, the method further comprises removing the second end cover prior to the step of inserting the distal body portion.

In some embodiments, the container includes a holding apparatus disposed therein, the method further comprising press fitting the proximal body portion to the proximal end of the holding apparatus. In such embodiments, the method may further comprise connecting the distal body portion to the proximal body portion without contacting the holding apparatus.

The container may include a holding apparatus disposed therein, and the method may further comprise connecting (e.g., press fitting) the distal body portion to the distal end of the holding apparatus. In such embodiments, the method may further comprise connecting the proximal body portion to the distal body portion without contacting the holding apparatus.

In some embodiments, the step of inserting the proximal body portion into the lumen comprises connecting (e.g., press fitting) the proximal body portion to the container. In some embodiments, the step of inserting the distal body portion into the lumen comprises press fitting the distal body portion to the container.

The step of inserting the proximal body portion may occur before the step of inserting the distal body portion. Alternatively, the step of inserting the distal body portion may occur before the step of inserting the proximal body portion.

As used herein the term "distal" refers to a direction toward the portion of an injector through which an IOL enters a patient's eye from the injector. As used herein the term "proximal" refers to a direction opposite of the distal direction.

BRIEF DESCRIPTION OF THE DRAWINGS

Illustrative, non-limiting embodiments of the present invention will be described by way of example with reference to the accompanying drawings, in which same reference numbers are used to designate same or similar components in different figures, and in which.

DETAILED DESCRIPTION

Figure 1:
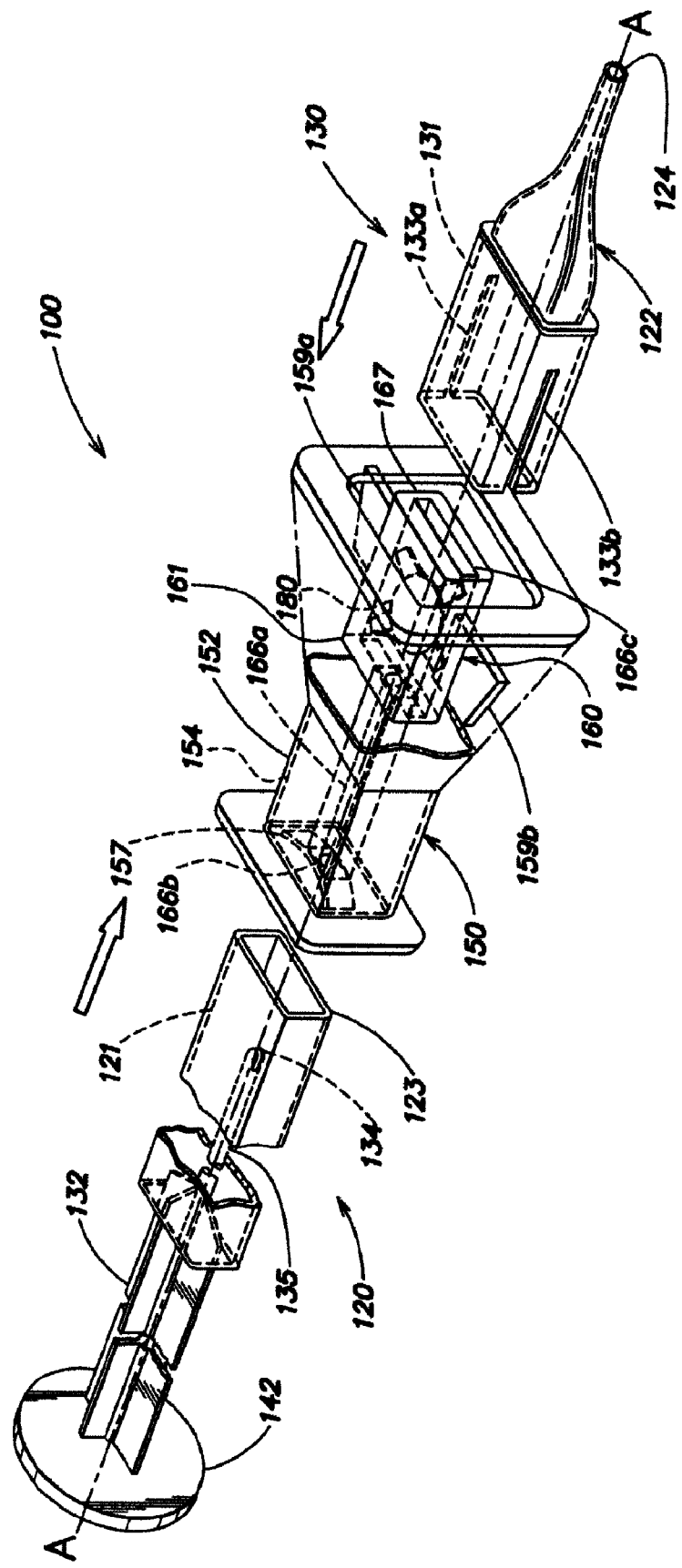
FIG. 1 is a perspective view of an example of an embodiment of an IOL injector in which a proximal body portion, a distal body portion, and a container are illustrated as separated from one another.

FIG. 1 is a perspective view of separated components of an example of an embodiment an IOL injector 100 according to aspects of the present invention. The IOL injector comprises proximal body portion 120, distal body portion 130, and a container 150 (e.g., a vial) that are capable of being coupled together. Proximal body portion 120 has a first lumen 121 disposed therethrough, and distal body portion 130 has a second lumen 131 disposed therethrough. Container 150 comprises a wall 152 defining a container lumen 154, a proximal open end 162 and a distal open end 164. The proximal open end is configured to receive the distal end 123 of proximal body portion into the container lumen. The distal open end is configured to receive the proximal end of the distal body portion into the container lumen. It is to be appreciated that an inserter kit having a container, a proximal body portion and a distal body portion so configured may offer advantages such as ease and consistency of assembly. The distal body portion may be inserted into the container lumen before the proximal body portion is inserted into the container lumen; alternatively, the proximal body portion may be inserted into the container lumen before the distal body portion is inserted into the container lumen.

In the illustrated embodiment, when the proximal body portion is inserted into the proximal open end and the distal body portion is inserted into the distal open end, a complete inserter is formed. It is to be appreciated that, in other embodiments additional components may be added to the inserter prior to operation of the inserter. For example, in some embodiments, a plunger 132 may be added after assembly of proximal body portion 120, distal body portion 130 and container 150. In other embodiments, as illustrated in FIG. 1, the plunger may be mounted to the proximal body portion at the time assembly. In some embodiments, a cartridge 122 is connected to the distal body portion after assembly of proximal body portion 120, distal body portion 130 and container 150.

In the illustrated embodiment, an IOL holding apparatus 160 is disposed inside the container to maintain the IOL. The holding apparatus has a proximal end 161 and the distal end 167. Proximal end 161 and the proximal body portion are configured such that the distal end of the proximal body portion couples to proximal end 161. Distal end 167 and the proximal end of the distal body portion are configured such that the distal body portion couples to distal end 167.

In the illustrated embodiments, cartridge 122 is suitably shaped to fold an IOL as the IOL passes through the cartridge. The IOL passes through the cartridge to an end 124 where the IOL is delivered into an eye. The end is sized to enter a relatively small incision in a patient's eye. Although the illustrated embodiment of the IOL injector includes a cartridge to fold and/or compress the IOL, an injector according to aspects of the present invention may be provided with no such apparatus. For example, a compressor drawer may be included to fold and/or compress the IOL.

Figure 3:
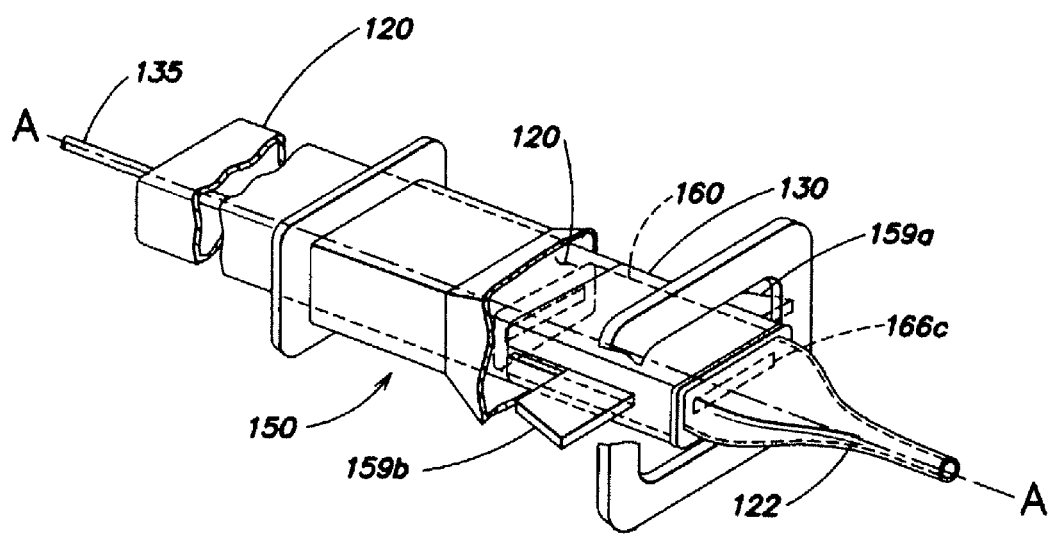
FIG. 3 is a perspective view of the embodiment of an IOL injector shown in FIG. 1 illustrated in an assembled state.

When the inserter is assembled (shown in FIG. 3), shaft 135 of plunger 132 is aligned along a longitudinal axis A-A. The first lumen 121 and second lumen 131 are aligned such that the plunger can extend through the first and second lumens during insertion. Insertion is achieved by actuation of plunger using thumb press 142. In some embodiments, the lumens are configured and arranged such that axis A-A extends substantially through the centers of the proximal body portion and the distal body portion. However, such an alignment is not necessary, and the centers may be offset from one another.

During actuation of the plunger, a tip 134 of the plunger pushes an IOL through the second lumen and into an eye through end 124. The tip may have any suitable configuration. For example the tip may be fork-shaped, flat, concave or convex; and the tip may be made of the same material as the plunger shaft or may be made of a relatively soft material such as silicone.

It is to be appreciated that proximal body portion 120 may have any suitable configuration such that a plunger is maintained prior to actuation, and such that the plunger can be actuated to push an IOL into an eye. In some embodiments, lumen 121 may be smaller in cross section than lumen 131. It is to be further appreciated that the smaller size of the proximal body portion is possible because the primary function of the proximal body portion is to maintain the plunger 132 prior to actuation and to allow the plunger to be actuated. Proximal body portion 120 can be rotationally complete such that lumen 121 is a closed structure. Alternatively, proximal body portion 120 can have one or more open portions where the plunger is not surrounded by the proximal body portion.

Figure 2:
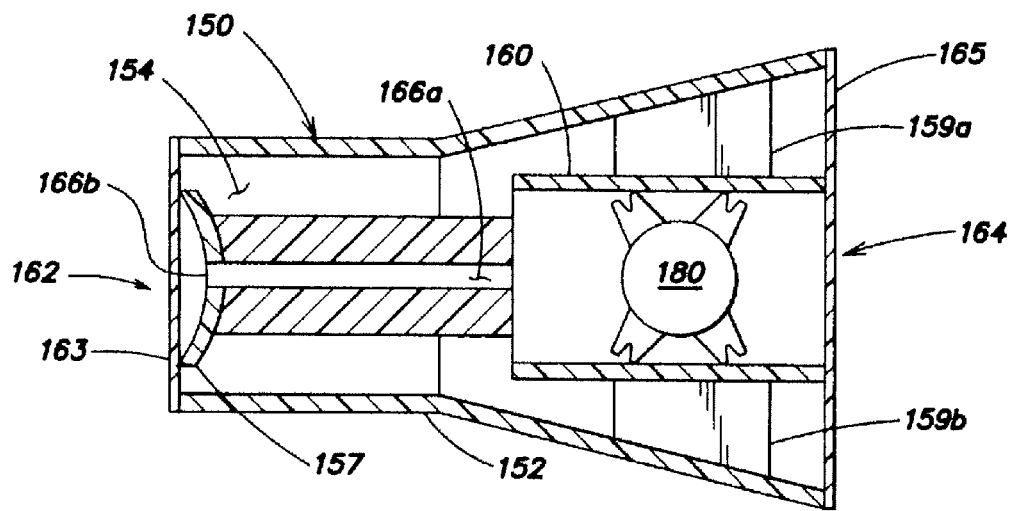
FIG. 2 is a cutaway section view of the example embodiment of a container shown in FIG. 1, illustrating further details of the container.

FIG. 2 is a cutaway section view of container 150 illustrating further details of container 150. Container 150 comprises a proximal end cover 163 and a distal end cover 165 configured and arranged to seal proximal open end 162 and distal open end 164, respectively.

An IOL 180 is disposed inside container 150. It is to be appreciated that, by sealing container 150, IOL 180 can be maintained sterile and/or hydrated. In embodiments in which the IOL is to remain hydrated, a fluid is sealed inside the container along with the IOL. Typically, the fluid is provided in sufficient quantity such that the IOL is immersed in the fluid regardless of the orientation of the container.

During assembly of an inserter, proximal end cover 163 is removed prior to the step of inserting the proximal body portion; and the distal end cover 165 is removed prior to the step of inserting the distal body portion. Although it is desirable in some embodiment that a container have end covers, in some embodiments of the present invention end covers may be omitted. It will be appreciated that the presence or absence of fluid within a container is determined at least in part on the material comprising the IOL stored in the container.

The holding apparatus is suspended inside of the container by connectors 159a and 159b. Distal body portion 130 is provided with slots 133a and 133b that slide over connectors 159a and 159b, respectively. IOL 180 may be maintained in a location within the container by any suitable holding apparatus 160 such that the plunger tip can urge the IOL into an eye upon actuation of the plunger.

The holding apparatus may provide a channel 166a for receiving plunger 132. During actuation of the plunger, the plunger extends through the channel, and plunger tip 134 displaces the IOL from the container into the distal portion, and then into an eye. In some embodiments, the proximal end 157 of holding apparatus 160 has a funnel shape leading to hole 166b, which guides the plunger tip into channel 166a.

A hole 166c is located at the distal end of the channel. Hole 166c is shaped to permit the IOL and the plunger to exit the holding apparatus and enter lumen 131 of distal body portion 130.

It is to be appreciated that although lumens 121, 131 and lumen 154 are illustrated as having rectangular cross sections, the shapes of the lumens may be any other suitable shapes such as rounded (e.g., circular or oval) or polygonal. Furthermore, lumens 121, 131 and 154 may have shapes that are different than one another.

The container, holding apparatus and injector body may be constructed to operate with a single-element IOL or a multi-element IOL. As illustrated in the embodiment shown in FIG. 3, proximal body portion 120 and distal body portion 130 are connected to holding apparatus 160 by press fitting proximal body portion 120 onto the proximal end of the holding apparatus and press fitting distal body portion 130 onto the distal end of holding apparatus 160. As discussed above, slots on distal body portion 130 slide over connectors 159a and 159b.

In some embodiments (not shown), the proximal and/or distal body portions, and the holding apparatus are configured such that connecting of the proximal and/or the distal body portions with the holding apparatus is achieved with a snap fit. In some embodiments, the distal body portion connects to the holding apparatus and the proximal body portion slides over the distal body portion (i.e., the proximal body portion couples to the holding apparatus (and therefore the container) without contacting the holding apparatus or any portion of the container). In some embodiments, the proximal body portion connects to the holding apparatus and the distal body portion slides over the distal body portion (i.e., the distal body portion couples to the container without contacting the holding apparatus or any other portion of the container). In some embodiments, the distal body portion and the proximal body portion connect to the container by press fit to the inner surface of the container lumen (e.g., without contacting the holding apparatus). Other structures for maintaining the proximal body portion and/or the distal body portion within the container may be used.

The injector components may be made of any suitable material, for example, polypropylene. In some embodiments, it is advantageous of the components are made of clear material to facilitate viewing of an IOL during assembly of an injector and injection of the IOL into a patient's eye.

Having thus described the inventive concepts and a number of exemplary embodiments, it will be apparent to those skilled in the art that the invention may be implemented in various ways, and that modifications and improvements will readily occur to such persons. Thus, the embodiments are not intended to be limiting and presented by way of example only. The invention is limited only as required by the following claims and equivalents thereto.

What is claimed is:

1. A method of loading an IOL injector with an IOL, the IOL injector comprising a proximal body portion and a distal body portion comprising:
   providing a container containing an IOL, the container comprising a first end of the container and a second end of the container, and a container lumen, providing the container in a sealed state, the container comprising a first end cover and a second end cover configured to seal said first end and said second end respectively;
   inserting the proximal body portion into the container lumen through the first end; inserting the distal body portion into the container lumen through the second end; removing the first end cover prior to the step of inserting the proximal body portion; and removing the second end cover prior to the step of inserting the distal body portion.

2. The method of claim 1, wherein the container includes a holding apparatus disposed therein, the method further comprises connecting the proximal body portion to the proximal end of the holding apparatus.

3. The method of claim 2, further comprising connecting the distal body portion to the proximal body portion without contacting the holding apparatus.

4. The method of claim 1, wherein the container includes a holding apparatus disposed therein, the method further comprises connecting the distal body portion to the distal end of the holding apparatus.

5. The method of claim 4, further comprising connecting the proximal body portion to the distal body portion without contacting the holding apparatus.

6. The method of claim 1, wherein the step of inserting the proximal body portion into the lumen comprises connecting the proximal body portion to the container.

7. The method of claim 1, wherein the step of inserting the distal body portion into the lumen comprises connecting the distal body portion to the container.

8. The method of claim 1, wherein the step of inserting the proximal body portion occurs before the step of inserting the distal body portion.

9. The method of claim 1, wherein the step of inserting the distal body portion occurs before the step of inserting the proximal body portion.

* * * * *